United States Patent [19]

Hoang

[11] Patent Number: 5,689,520
[45] Date of Patent: Nov. 18, 1997

[54] METHOD AND APPARATUS FOR VARIABLE WAVEFORM OUTPUT IN SURGICAL LASERS

[75] Inventor: Anh N. Hoang, San Jose, Calif.

[73] Assignee: Xintec Corporation, Oakland, Calif.

[21] Appl. No.: 550,631

[22] Filed: Oct. 31, 1995

[51] Int. Cl.$^6$ .................................................... H01S 3/00
[52] U.S. Cl. .................................................... 372/38; 372/25
[58] Field of Search .................................................... 372/25, 30, 38

[56] References Cited

U.S. PATENT DOCUMENTS

| | | | |
|---|---|---|---|
| 4,630,277 | 12/1986 | Cirkel et al. | 372/38 |
| 4,724,835 | 2/1988 | Liss et al. | 372/38 |
| 4,763,336 | 8/1988 | Stephens | 372/38 |
| 4,785,456 | 11/1988 | Kaplan | 372/38 |
| 4,950,268 | 8/1990 | Rink | 372/38 |
| 5,072,191 | 12/1991 | Nakajima et al. | 372/38 |
| 5,255,277 | 10/1993 | Carvalho | 372/38 |
| 5,280,536 | 1/1994 | Dumond et al. | 372/38 |
| 5,363,387 | 11/1994 | Sinofsky | 372/15 |

OTHER PUBLICATIONS

Product Prochure: VersaPulse Select: Holmium and Nd:YAG Combination laser for Urology, Coherent, Inc., copyright 1994, 8 pages, No Month.

Primary Examiner—Rodney B. Bovernick
Assistant Examiner—Robert E. Wise
Attorney, Agent, or Firm—Ray K. Shahani

[57] ABSTRACT

Variable waveform output in surgical laser is achieved by controlling power into a solid-state laser cavity. A control circuit is used to coordinate pulse energy, pulse frequency, and pulsewidth into a solid-state laser cavity to achieve a user desired waveform output. An Insulated Gate Bipolar Transistor (IGBT) or similar solid-state transistor switching device under the direction of a control circuit is used to switch energy into the solid-state laser cavity thereby modulating the pulse frequency and pulsewidth. The pulse energy is varied by varying the charge across the capacitor bank which sends energy through the IGBT to the solid-state laser cavity. By having the ability to vary the laser's output pulse frequency, pulsewidth, and pulse energy, multiple tissue effects can be achieved using one solid-state laser cavity.

14 Claims, 2 Drawing Sheets

METHOD AND APPARATUS FOR VARIABLE WAVEFORM OUTPUT IN SURGICAL LASERS

FIELD OF THE INVENTION

The present invention relates to control circuits for surgical lasers and more specifically to methods and devices for producing a variable waveform output in surgical lasers.

BACKGROUND OF THE INVENTION

The predominate prior-art in pulsing solid state lasers for use in laser surgery incorporate a fixed pulsewidth output. Pulsewidth is defined by the time duration of a single laser pulse which is on the order of 1 microsecond to 1 millisecond. Fixed pulsewidth lasers use a Pulse Forming Network (PFN) comprising of inductors and capacitors. The value of these passive elements are chosen for a desired pulse output and can not be adjusted by the end-user. The frequency of the pulses are controlled via a Silicon Controlled Rectifier (SCR) through user input. Fixed pulsewidth lasers are acceptable when the laser systems are used in very specific applications for which the pulsewidth has been previously determined.

Conventionally, Q-switched lasers employ solid state crystals or other gain media within a cavity to modulate laser resonance. The gain medium stores the energy until a triggering signal or other threshold event causes the energy to be released as a large pulse. For example, the medium or switch can be an accousto-optical or electro-optical crystal which switches the "Q" of the cavity between a high value which supports lasing action with the resonant cavity and a low value which essentially turns off the resonant cavity. While the switch is turned off, the pumping energy builds a population inversion within the cavity. When the Q-switch is turned on, the built-up population inversion is rapidly discharged, resulting in a large pulse of laser energy.

In such conventional Q-switched laser systems, there is typically little or no control over pulsewidth. The pulsewidth is largely dependent on the cavity, itself, and the switching repetition rate. Moreover, conventional Q-switched laser systems are often il-suited for production of very long laser pulses, e.g., on the order of 10 milliseconds or longer.

In the past, due to the limited applications of surgical lasers, fixed pulsewidth lasers were acceptable. But due to the increasing interest in laser surgery, and recent FDA clearances, there has been renewed interest in a more versatile surgical laser. One method to increase the flexibility of a laser system is by having the ability to vary the wave form output, including variable pulsewidths. Typically, for fragmenting urinary and biliary calculi, pulsewidths of about 350 microseconds at about 5 to 10 hertz delivering 0.5 to 1.0 joules of energy per pulse have been successfully employed. For cutting or ablating soft tissue, pulsewidths of about 250 to 350 microseconds at about 5 to 15 hertz delivering 0.5 to 2.0 joules of energy per pulse have been successfully employed whereas for coagulating tissue, pulsewidths of about 500 to 700 microseconds at about 5 to 15 hertz delivering 0.5 to 2.0 joules of energy per pulse have been successfully employed. For orthopedic applications, pulsewidths of about 350–500 microseconds at about 5 to 40 hertz delivering 0.5 to 4.0 joules of energy per pulse have been successfully employed. As in almost all surgical applications, the surgeon or physician performing the operation has ultimate control over the actual operating parameters employed in a given surgical procedure, and the above mentioned parametes are intended for illustrative purposes only.

One approach to providing a surgical laser with greater adaptability and flexibility to different surgical applications has been to provide a surgical laser system having a dual wavelength output. Such a system could combine the Nd:YAG laser having a wavelength of 1.06 microns for deep coagulation and hemostasis with a Holmium laser providing a 2.1 micron energy beam for precise cutting, fragmentation or ablation. However, though a single piece of equipment serves a broad range of uses, the complexity and cost associated with such a dual wavelength system is considerable. There remains a need for a less complicated, single wavelength laser with greater adaptability at a lower cost.

Though it is possible to convert prior-an fixed pulsewidth laser systems to generate variable pulsewidth, it is often not practical. One such method to vary pulsewidth in a PFN is to vary the inductance in the inductor. This method requires a parallel inductor circuit which connects and disconnects inductors to adjust the pulsewidth. This method requires more inductors, thus adding to the weight and complexity of the entire system. Inductors being energy storage elements need to be charged before discharging so rapid variations in pulsewidth can not be achieved with a PFN.

Another method to achieve variable laser output pulsewidth is through an oscillating reflector within the laser cavity (U.S. Pat. No. 5,363,387). Laser energy leaves the laser cavity only when the oscillating sweep path matches the resonant conditions of the specific laser. By varying the oscillations of the reflector, lasers pulses of different duration can be generated. The oscillating reflector method requires a continuous wave (CW) laser to be effective. This method can be energy inefficient, because in pulsing mode, energy normally leaving the cavity is trapped and dissipated into heat. Also oscillating reflectors and its associated optics are complicated and expensive to implement. Furthermore, the resonance required between the oscillating sweep of the reflector and the wave of laser radiation limits the actual variability of the pulsewidth to a set of discrete operating parameters, as a function of the control mechanism on the oscillating reflector.

Presently there exists a need to obtain a variable pulse waveform that is both continually variable over a broad band of pulsewidths and frequencies and inexpensive to implement. In addition to variable pulsewidth and variable frequency, variable pulse energy, often referred to as pulse peak power, can be added to further increase user flexibility. By having the ability to vary pulsewidth, frequency, and magnitude, any output function can be generated within the capability of the system.

SUMMARY OF THE INVENTION

The present invention generally comprises of an Insulated Gate Bipolar Transistor (IGBT), or similar solid-state transistor, which is controlled by a microprocessor-based control circuit. Power received from the power supply may be rectified and directed to charge one or more DC storage elements, such as a capacitor. Energy is discharged from the capacitors to the solid-state laser cavity only when the IGBT is switched on. The control circuit contains two output channels: one analog signal to regulate power levels into the power supply and one digital signal to control the IGBT. By regulating both frequency, magnitude, and pulsewidth, virtually any laser waveform can be generated.

The control circuit, in order to deliver consistent output at the point of delivery (i.e. the distal end of the fiber-optic delivery system), receives feedback between pulse intervals. This information will aid the control system in determining the magnitude and pulsewidth for the next pulse to compensate for initial overshoot or undershoot. On average, the total energy delivered to the surgical site should match very closely to user input.

By having the ability to define and regulate laser output, multiple tissue effects can be achieved. Although the preferred embodiment is described with respect to medical applications, it may be appreciated that the attributes of the laser system of the present invention could be directed to industrial, scientific, and other commercial uses in which deliberate and precise application of laser energy is useful.

Furthermore, the present invention allows for relatively easy conversion of an existing fixed pulsewidth laser to a variable waveform laser. Unlike some variable pulsewidth prior-art laser systems, the present invention modulates the pulsewidth, frequency, and magnitude by input power to the cavity alone thereby leaving existing laser cavity, optics, and delivery systems unchanged. Because of the present invention's ability to modulate power between pulses, a realtime feedback loop was included to insure that the actual output to the target site matches user input instead of assuming power input into the capacitors equals laser output. This assumption is often false due to the time delay of the devices (i.e. charging the capacitors), tolerances of the components, and other losses between the laser cavity and the distal end of the fiber-optic delivery system.

The present invention, by having the ability to adjust each pulse in real-time, opens the possibility to produce a series of pulses with varying magnitude. When grouped together, a nonlinear distribution of energy is produced within the "pulse envelope." Through experimentation, an optimum "pulse envelope" can be derived to create desired tissue effect for a specific application. The present invention through proper programming has the ability to perform delicate surgical laser procedures such as in the brain or heart in addition to any other application cleared by the Food and Drug Administration.

Numerous other advantages and features of the present invention will become readily apparent from the following detailed description of the invention and the embodiments thereof, from the claims and from the accompanying drawings in which the details of the invention are fully and completely disclosed as a pan of this specification.

DETAILED DESCRIPTION OF THE INVENTION

Figure 1:
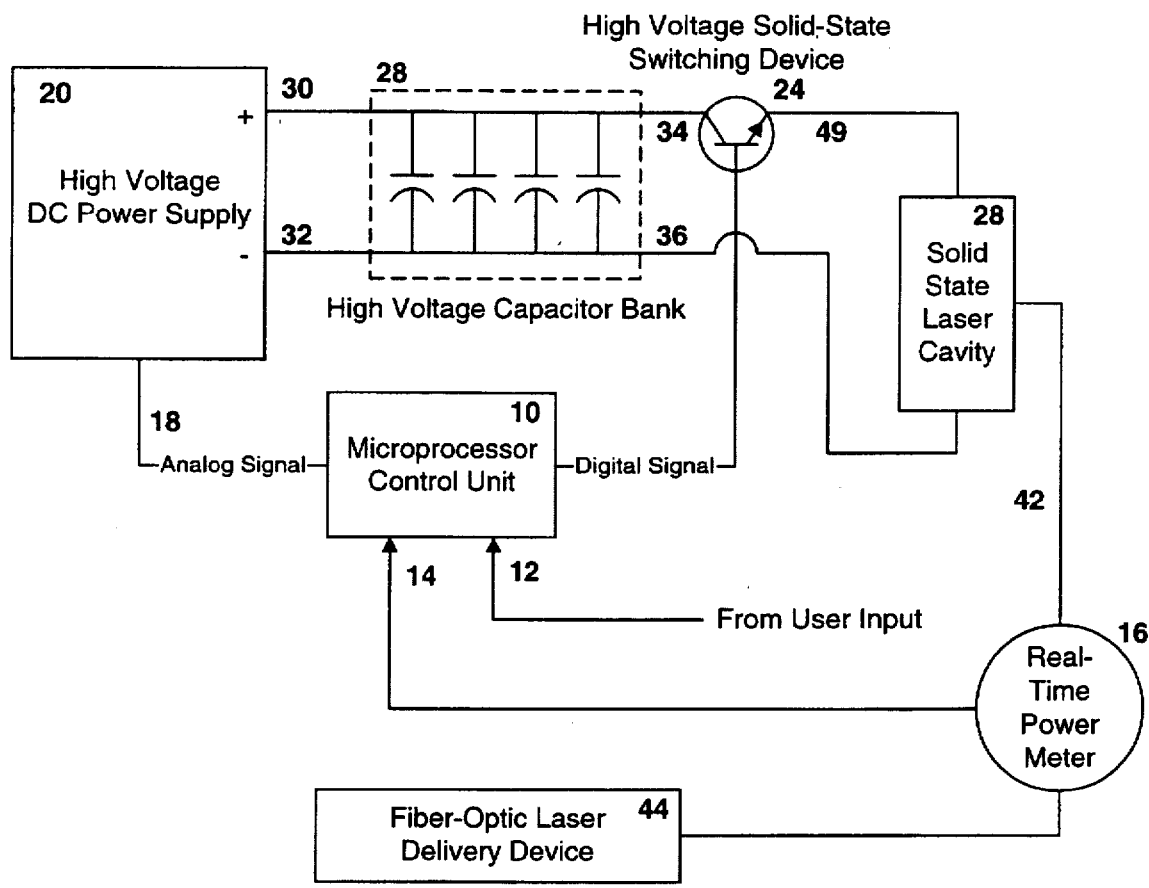
FIG. 1 is a schematic representation of a variable waveform circuit of an embodiment of the present invention.

FIG. 1 is a schematic representation of a variable waveform circuit of an embodiment of the present invention. The microprocessor-based control unit 10 receives two inputs—a user input 12 from a user and another, real-time power signal 14 from a real-time power meter 16. The microprocessor-based control unit produces two output signals—one, a low-voltage power supply control signal 18 to control the high-voltage power supply 20 and another, a low-voltage solid-state switching device control signal 22 to control the high-voltage solid-state switching device 24. In a preferred embodiment, the low-voltage power supply control signal is an analog signal whereas the low-voltage solid-state switching device control signal is a digital signal. The high-voltage solid-state switching device receives the low-voltage solid-state switching device control signal from the microprocessor-based control unit, switching it either on or off, thereby regulating power into the solid-state laser cavity 26.

When the high-voltage power supply, supplying a direct current in a preferred embodiment, receives the low-voltage power supply analog control signal from the microprocessor-based control unit, it regulates the voltage charging the high-voltage capacitor bank 28 across the two capacitor bank input leads 30 and 32. This capacitor bank can be any power storage source suitable for the given application, and it will be understood that the capacitor bank is but one possibility for a storage device performing a similar function. During operation, the capacitor bank is allowed to develop a high-voltage potential which develops across the output leads 34 and 36. One of the leads is connected to a common ground 38 while the other output lead is connected to the input of the high-voltage side of the high-voltage solid-state switching device. Thus, when the low-voltage switching device control signal from the microprocessor-based control unit signals the switching device to open, a pulse of high-voltage energy is switched to the laser cavity through the output 40 of the high-voltage side of the switching device.

As the laser cavity becomes charged with energy received through the high-voltage solid-state switching device and beings to resonate, output laser energy 42 from the laser cavity can be directed to a fiber optic laser delivery device 44. It will be understood that this fiber optic laser delivery device can be replaced with any suitable type of laser energy delivery device, such as a single fiber optic cable, a fiber optic cable with a firing tip, a plurality of optical fibers or optical fiber delivery devices, or any other suitable laser energy delivery system. In a preferred embodiment, it is desirable to place the real-time power meter disposed within the stream of output laser energy. This power meter will read the power level of the resulting pulse of energy produced by the laser cavity and send the low-voltage real-time power meter signal to the microprocessor-based control unit.

After each pulse of energy id delivered to the laser cavity and the real-time power meter measures the actual power produced by the laser cavity, the microprocessor-based control unit receives feedback from the real-time power meter to determine if the output of the laser cavity matched the user-specified input. The software embedded in the microprocessor-based control unit will compensate for overshoot and undershoot with the next succeeding pulse, and a user-defined output from the laser cavity can be produced and manipulated by a surgeon as the lasing parameters of a particular medical operation or other application dictate.

Figure 2:
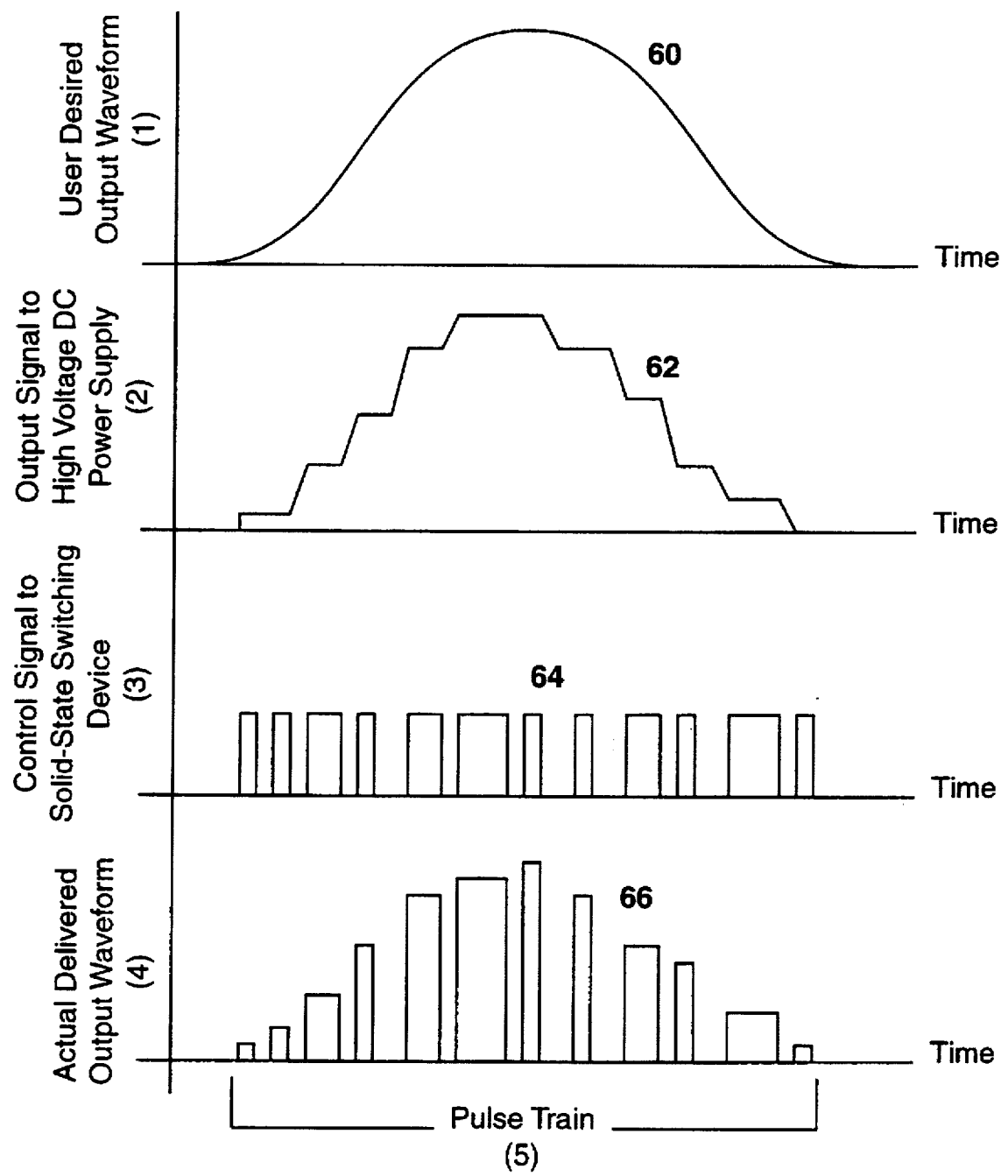
FIG. 2 is an example of a timing sequence for a "pulse train" of an embodiment of the present invention.

FIG. 2 is an example of a timing sequence for a "pulse train" of an embodiment of the present invention. The diagram illustrates the analog signal being sent to the high-voltage DC power supply and the timing pulse, which includes the pulsewidth, and frequency, being sent to the solid-state transistor. The combined effect is a "pulse train" that resembles very closely the desired output. Referring to output waveform 60. Turns the laser control system with a desired output waveform 60. The parameters of this desired user-input waveform would include frequency, pulsewidth and/or integrated power output. The microprocessor then processes this user-input desired waveform along with any real-time power meter information already produced by the real-time power meter (if any) and produces the two output signals from the microprocessor-based control unit. These two outputs are then split into two channels: one for magnitude and the other for pulsewidth and frequency. The low-voltage power supply control signal is sent to the high-voltage power supply which begins to charge the capacitor bank to the desired voltage. This low-voltage power supply control signal is represented by curve 62. Simultaneously, a digital, low-voltage control signal represented by curve 64 is sent to the high-voltage solid-state switching device to switch it on and off. When the switch is on, energy with a magnitude determined from the charged capacitors is sent to the solid-state laser cavity for a duration determined by the digital signal to the switching device. The combination of the charge across the laser cavity having an amplitude determined by the charge on the capacitor bank, switched across the laser cavity for a duration and at a frequency as determined by the digital control signal from the microprocessor-based control unit acting upon the low-voltage input side of the switching device, results in an actual delivered output waveform represented by curve 66. Thus, with control signals represented by curves 62 and 64, the magnitude, pulsewidth and frequency of laser energy actually delivered by a fiber optic laser delivery device, represented by curve 66, can be made to closely resemble the laser's desired output, as represented by curve 60, both in power distribution and total energy delivered.

It will be obvious that the actual waveform output can be any combination of pulse energy, pulsewidth, and pulse frequency. The number of possible combinations is limited only by the operating specifications of the components of the system. Certain combinations of the above parameters can yield interesting results. For example, by using a very long pulsewidth or near infinite pulse frequency (i.e. simulating continuous wave), the output waveform can be matched with the control signal to the high-voltage DC power supply. By fixing the pulse energy, uniform magnitude pulses with varying pulsewidth and frequency can be achieved. By having the ability to vary the actual waveform output, and by applying the present invention to different solid-state wavelength lasers, surgical effects never before possible never before possible on tissue and other material can be achieved.

It will be apparent to those skilled in the art that the high-voltage power supply could be any power supply suitable for charging a laser cavity with sufficient energy to induce laser energy production from the cavity. This could be a direct-current power supply, an alternating current power supply, etc. and might contain one or more rectifiers, diodes, etc.

It will be apparent to those skilled in the art that the high voltage switching device could be any one of a number of devices capable of switching a high-voltage across the laser cavity repeatedly, rapidly and efficiently. Typical devices used are insulated-gate bipolar transistor-type (IGBT) switches, MOSFET switches, various silicon-controlled rectifiers and other types of solid-state or non-solid-shale switching devices. Typical IGBT switches can switch currents of up to about 1200 ampers at rates of about 100 kilohertz while MOSFET switches operate at rates of up to about 1 megahertz at maximum switching loads of about 50 amperes. It will be understood that new technological advances in operating speeds and peak loads and limits and other operational parameters of solid-state and other electronic devices will greatly enhance the operability and field of applicability of the current invention.

It will be apparent to those skilled in the art that the capacitor bank is essentially a high-voltage power storage element. The term capacitor bank is intended to mean any of a multiplicity of storage element designs and may be used interchangeably herein with other terms such as capacitor array, high-voltage power storage element, plurality of capacitors, etc. This capacitor bank could include one or more capacitors in parallel or series, and could also include other circuit elements, including rectifiers, diodes, controllers, inductors, resistors, measuring devices for monitoring or measuring the charge on the power storage element, safety and integrity maintaining devices, and other control elements.

It will be apparent to those skilled in the art that the control unit used to combine the user input information with the measurements taken from the power meter and thus produce control signals for the power supply and the switching device could be a microprocessor-based control unit, a fully programmable computer, an EEPROM or other system for performing the necessary algorithms and functions on the measured and selected inputs and input signals in order to produce the necessary output control signals.

A preferred embodiment of the present invention has a variable pulsewidth range. A more preferred embodiment of the present invention has a variable pulsewidth range between about 250 and 1000 microseconds. A most preferred embodiment of the present invention has a variable pulsewidth range between about 250 and 700 microseconds.

A preferred embodiment of the present invention has a variable laser output power. A more preferred embodiment of the present invention has a variable laser output power of between about 100 watts to about 10 kilowatts. A most preferred embodiment of the present invention has a variable laser output power of between about 5 and 6 kilowatts.

Thus, the present inveniton, while suitable for use with a range of different types of lasers, including holmium lasers and Nd:YAG lasers and others, will allow stone fragmentation using pulsewidths of about 350 microseconds, cutting and ablation of tissue at lower pulsewidths such as 250, 350 or 500 microseconds, and coagulation of tissue at pulsewidths of about 500, 700 or 1000 microseconds.

The user interface can be any of a variety of different types of interfaces which will be known to those skilled in the art. One preferred embodiment would include a touch-screen type control panel with a certain configuration. The configuration would allow the user to set the energy rate per pulse and/or repetition rate or number of pulses per second. The average power could be calculated automatically. A Joules or other unit of energy display will display the total energy delivered in real time. In one embodiment, an energy or Joules preset could initiate a count down in energy or Joules. When the energy or total Joules is preset, the countdown automatically begins when the laser is activated. When the counter reaches zero, the laser will return to standby mode. The user can touch the screen to repeat the operation. Other types of user interfaces include control via a personal computer or other microprocessor.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A variable waveform output laser system, the laser system having a laser cavity, the laser cavity containing a gain medium which produces a laser output upon stimulation, the laser output having a predetermined variable waveform, the waveform of the laser output being determined by a user's input to the laser system specifying the pulsewidth, frequency and/or amplitude of the laser output, the laser system comprising:

a high-voltage power supply, the power supply capable of inducing stimulation of the gain medium of the laser cavity, the power supply having a first terminal and a second terminal, the power supply being controlled by a control signal;

a high-voltage switching device, the switching device capable of rapidly and efficiently opening and closing a high-voltage circuit, the switching device disposed between the power supply and the laser system, the switching device having a high side and a low side, the high side of the switching device having an input and an output, the low side of the switching device having an input, the input of the low side being a control signal for the switching device, the input of the high side of the switching device being connected to the first terminal of the power supply, the output of the high side of the switching device being connected to the laser cavity for stimulation of the laser gain medium;

a real-time power meter, the meter connected to the laser system for measuring the laser output, the meter producing an output control signal proportional to the laser output pulsewidth, frequency and/or amplitude;

a microprocessor-based control unit, the control unit having a first input and a second input, the control unit producing a first control signal and a second control signal, the first input to the control unit being from a user interface, the second input to the control unit being the output control signal produced by the meter, the first control signal from the control unit for controlling the power supply, the second control signal from the control unit for controlling the switching device;

a high-voltage power storage element, the storage element disposed between the power supply and the switching device, the storage element receiving a charge from the power supply and delivering that charge through the switching device to the laser cavity such that the gain medium is stimulated to produce the predetermined variable waveform output of the laser system, whereby the user's input to the laser system will be processed by the control unit which in turn will send control signals to the power supply and the switching device, thus resulting in a predetermined variable waveform output of the laser system.

2. The invention of claim 1 wherein the switching device is a solid-state switching device.

3. The invention of claim 2 wherein the solid-state switching device is an insulated gate bipolar transistor-type switching device.

4. The invention of claim 2 wherein the solid-state switching device is a MOSFET-type switching device.

5. The invention of claim 1 wherein the power storage element is comprised of a plurality of capacitors.

6. The invention of claim 1 wherein the first control signal produced by the control unit is an analog signal for controlling the power supply.

7. The invention of claim 1 wherein the second control signal produced by the control unit is a digital signal for controlling the switching device.

8. The invention of claim 1 wherein the predetermined variable waveform output of the laser system has a variable pulsewidth.

9. The invention of claim 1 invention the predetermined variable waveform output of the laser system has a variable pulsewidth of between about 250 and about 1000 microseconds.

10. The invention of claim 1 wherein the predetermined variable waveform output of the laser system has a variable pulsewidth of between about 250 and about 750 microseconds.

11. The invention of claim 1 wherein the predetermined variable waveform output of the laser system has a variable power output.

12. The invention of claim 1 wherein the predetermined variable waveform output of the laser system has a variable power output of between about 100 watts and about 10 kilowatts.

13. The invention of claim 1 wherein the predetermined variable waveform output of the laser system has a variable power output of between about 5 kilowatts and about 6 kilowatts.

14. A variable waveform laser output circuit for producing a predetermined variable waveform output having user-specified pulsewidth, frequency and/or amplitude values in a laser system comprising:

a power switching circuit including:
      a high-voltage power supply;
      a high-voltage switching device, the switching device in series with the power supply;
      a high-voltage power storage element in parallel with the power supply disposed between the power supply and the switching device; and a control circuit including:
      user input, the user input comprised of information specifying the pulsewidth, frequency and/or amplitude characteristics of the predetermined variable waveform output;
      a real-time power meter for measuring the real-time power output of the laser system, the meter producing a real-time power signal; and
      a control unit for processing the user input information along with the real-time power signal, the control unit producing a power supply control signal for controlling the power supply of the power switching circuit, the control unit producing a switching device control signal for controlling the switching device of the power switching circuit, whereby the power switching circuit is controlled by the control circuit such that the predetermined variable waveform output of the laser system is essentially identical with the user-specified pulsewidth, frequency and/or amplitude characteristics desired.

* * * * *